(12) United States Patent
Morello

(10) Patent No.: US 7,396,327 B2
(45) Date of Patent: Jul. 8, 2008

(54) BLOOD PUMP SYSTEM AND METHOD OF OPERATION

(75) Inventor: Gino F. Morello, Leonia, NJ (US)

(73) Assignee: Micromed Technology, Inc., Houston, TX (US)

( * ) Notice: Subject to any disclaimer, the term of this patent is extended or adjusted under 35 U.S.C. 154(b) by 944 days.

(21) Appl. No.: 10/675,669

(22) Filed: Sep. 30, 2003

(65) Prior Publication Data

US 2004/0215050 A1    Oct. 28, 2004

Related U.S. Application Data

(63) Continuation-in-part of application No. PCT/US03/00273, filed on Jan. 7, 2003, application No. 10/675,669, and a continuation-in-part of application No. PCT/US03/00516, filed on Jan. 8, 2003, application No. 10/675,669, and a continuation-in-part of application No. PCT/US03/18859, filed on Jun. 13, 2003, application No. 10/675,669, and a continuation-in-part of application No. PCT/US03/20268, filed on Jun. 26, 2003.

(60) Provisional application No. 60/319,358, filed on Jun. 26, 2002, provisional application No. 60/319,318, filed on Jun. 14, 2002, provisional application No. 60/346,555, filed on Jan. 8, 2002, provisional application No. 60/346,721, filed on Jan. 7, 2002.

(51) Int. Cl.
*A61N 1/362* (2006.01)
(52) U.S. Cl. .......................... 600/17; 623/3.1; 415/900
(58) Field of Classification Search ............. 600/16–18; 623/3.1–3.3; 415/900

See application file for complete search history.

(56) References Cited

U.S. PATENT DOCUMENTS

| | | | |
|---|---|---|---|
| 4,221,543 A | 9/1980 | Cosentino et al. |
| 4,363,609 A | 12/1982 | Cosentino et al. |
| 4,557,673 A | 12/1985 | Chen et al. |
| 4,578,077 A | 3/1986 | Joh |
| 4,692,145 A | 9/1987 | Weyant |
| 4,957,504 A | 9/1990 | Chardack |
| 5,041,086 A | 8/1991 | Koenig et al. |
| 5,511,958 A | 4/1996 | Chen et al. |
| 5,527,159 A | 6/1996 | Bozeman, Jr. et al. |
| 5,599,173 A | 2/1997 | Chen et al. |
| 5,888,242 A | 3/1999 | Antaki et al. |
| 5,947,892 A | 9/1999 | Benkowski et al. |
| 5,975,126 A | 11/1999 | Bump et al. |
| 6,066,086 A | 5/2000 | Antaki et al. |
| 6,183,412 B1 | 2/2001 | Benkowski et al. |
| 6,605,032 B2 | 8/2003 | Benkowski et al. |
| 2003/0069465 A1 | 4/2003 | Benkowski et al. |

FOREIGN PATENT DOCUMENTS

| | | |
|---|---|---|
| WO | WO 88/03784 | 6/1988 |
| WO | WO 00/19097 | 4/2000 |
| WO | WO 2004/054641 A1 | 7/2004 |

*Primary Examiner*—Scott M Getzow
(74) *Attorney, Agent, or Firm*—Locke Lord Bissell & Liddell LLP

(57) ABSTRACT

A blood pump system includes a blood pump having a motor with a rotor and a stator. The stator has a plurality of stator windings situated therein. A motor controller is coupled to the motor, and a processor has inputs coupled to the motor controller for receiving a time continuous signal from the pump. The processor is programmed to transform the time continuous signal to the frequency domain, and control the pump and detect excess suction in response to the time continuous signal in the frequency domain.

31 Claims, 13 Drawing Sheets

FIG. 7A CONSTANT SPEED

| CONTROL | SPEED LIMIT/ALARM | | POWER | FLOW | | SUCTION | | SUCTION DETECTION |
|---|---|---|---|---|---|---|---|---|
| VARIABLE | MIN | MAX | MAX | MIN | MAX | DETECTION | | RESPONSE |
| ENTER SPEED | 7.5k | N/A | 15W | ENTER MIN | N/A | ENABLED/DISABLED | | ENABLED/DISABLED |

FIG. 7B CONSTANT FLOW

| CONTROL | SPEED LIMIT/ALARM | | POWER | FLOW | | SUCTION | | SUCTION DETECTION |
|---|---|---|---|---|---|---|---|---|
| VARIABLE | MIN | MAX | MAX | MIN | MAX | DETECTION | | RESPONSE |
| ENTER FLOW | 8.0k | 11.0k | 8+FLOW*1.5 | FLOW*.75 | N/A | ENABLED | | ENABLED |

FIG. 7C CONSTANT WAVINESS

| CONTROL | SPEED LIMIT/ALARM | | POWER | FLOW | | SUCTION | | SUCTION DETECTION |
|---|---|---|---|---|---|---|---|---|
| VARIABLE | MIN | MAX | MAX | MIN | MAX | DETECTION | | RESPONSE |
| P2P = 4 | 8.0k | 11.0k | 8+FLOW*1.5 | ENTER MIN | N/A | ENABLED | | ENABLED |

FIG. 7D MAXIMIZE FLOW - WAVINESS (P2P)

| CONTROL | SPEED LIMIT/ALARM | | POWER | FLOW | | SUCTION | ALLOW FLOW |
|---|---|---|---|---|---|---|---|
| VARIABLE | MIN | MAX | MAX | MIN | MAX | DETECTION/RESPONSE | BELOW BASELINE** |
| P2P = 2 *** | 9.0k | 12.0k | 18 | IMPORTED | N/A | ENABLED/ENABLED | ENABLED/DISABLED |

FIG. 7E MAXIMIZE FLOW - dQ/dN (DIMINISHING RETURNS)

| CONTROL | SPEED LIMIT/ALARM | | POWER | FLOW | | SUCTION | ALLOW FLOW |
|---|---|---|---|---|---|---|---|
| VARIABLE | MIN | MAX | MAX | MIN | MAX | DETECTION/RESPONSE | BELOW BASELINE** |
| dQ/dN | 9.0k | 12.0k | 18 | IMPORTED | N/A | ENABLED/ENABLED | ENABLED/DISABLED |

BLOOD PUMP SYSTEM AND METHOD OF OPERATION

CROSS-REFERENCE TO RELATED APPLICATIONS

This application is a continuation-in-part of International Application No. PCT/US03/00273 (Jan. 7, 2003), which is a non-provisional of U.S. Provisional Application No. 60/346,721 (Jan. 7, 2002); International Application No. PCT/US03/00516 (Jan. 8, 2003), which is a non-provisional of U.S. Provisional Application No. 60/346,555 (Jan. 8, 2002); International Application No. PCT/US03/18859 (Jun. 13, 2003), which is a non-provisional of U.S. Provisional Application No. 60/319,318 (Jun. 14, 2002); and International Application No. PCT/US03/20268 (Jun. 26, 2003), which is a non-provisional of U.S. Provisional Application No. 60/319,358 (Jun. 26, 2002). Each of the applications referenced above is incorporated by reference herein.

BACKGROUND

1. Field of the Disclosure

The disclosure relates generally to blood pump systems, and more specifically, to a method and system for control of such pumps.

2. Description of Related Art

Generally, blood pump systems are employed in either of two circumstances. First a blood pump may completely replace a human heart that is not functioning properly, or second, a blood pump may boost blood circulation in patients whose heart is still functioning although pumping at an inadequate rate.

For example, U.S. Pat. No. 6,183,412, which is commonly assigned and incorporated herein by reference in its entirety, discloses a ventricle assist device (VAD) commercially referred to as the "DeBakey VAD™." The VAD is a miniaturized continuous axial-flow pump designed to provide additional blood flow to patients who suffer from heart disease. The device is attached between the apex of the left ventricle and the aorta. Proper blood flow through the device depends on an adequately filled ventricle and a positive differential pressure between the inlet and the outlet of the VAD pump.

Known blood pump systems typically are controlled in an open loop fashion where a predetermined speed is set and the flow rate varies according to the pressure differential across the pump. The pump itself may be controlled in a closed loop fashion, wherein the actual pump speed is fed back to a motor controller that compares the actual speed to the desired predetermined speed and adjusts the pump accordingly. However, prior art closed loop control systems—varying the pump speed in response to a monitored physiologic parameter—have largely been unsatisfactory.

Moreover, since the VAD produces flow continually and actively fills, it has the potential to create low pressure at the inflow in order to produce flow. "Excess Suction" occurs when the pressure in the inflow cannula decreases significantly—the pump begins to "suck" the ventricle closed, which would greatly reduce the pumping capability of the native heart and VAD. Decreasing the VAD's speed during an excess suction condition would allow the ventricle to refill, and normal blood flow to resume. Additionally, the detection of ventricular collapse and the ability to automatically adjust the pump's speed may aid in maintaining correct blood flow to the patient.

Excess suction may be caused by occlusion of the tip of the inflow cannula or by completely emptying the ventricle (ventricular collapse). In known pump systems, sustained excess suction typically triggers a diagnostic alarm on the pump controller. However, it would be desirable to detect the onset of suction prior to any physiological effect. Additionally, it is typical of known methods that attempt to detect the onset or presence of ventricular collapse to use a binary "suction detect" flag when the onset of suction is believed to have been discovered. Information in addition to a simple binary indicator, however, is desirable as it would allow a physician or technician to make a more precise diagnosis.

The present invention addresses shortcomings associated with the prior art.

SUMMARY OF THE DISCLOSURE

In one aspect of the present disclosure, a blood pump system includes a blood pump having a motor with a rotor and a stator. The stator has a plurality of stator windings situated therein. A motor controller is coupled to the motor, and a processor has inputs coupled to the motor controller for receiving time continuous signals from the pump, such as flow, current, speed, etc. The processor is programmed to transform the time continuous signal(s) from the time domain to the frequency domain, and control the pump and to detect excess suction in response to the time continuous signal in the frequency domain.

The time continuous signal may include the stator winding current, the pump speed or the pump voltage, for example. In certain embodiments, the blood pump system includes a flow measurement device coupled to the processor for providing a signal representing the pump flow rate, wherein the time continuous signal may also include the pump flow rate.

In accordance with additional aspects of the disclosure, the processor may also be programmed to determine and output parametric data (mean values of flow, speed, heart rate, etc.) based on the sampled time continuous signal in the frequency domain. For example, heart rate may be derived from the frequency domain representation of the flow data. To obtain the desired resolution of the heart rate calculation within required time limits, the sampled time continuous signal may be zero padded. Still further, the processor may be programmed to validate integrity of the sampled time continuous signal based on the sampled time continuous signal in the frequency domain. This validation may include calculating the signal to noise ratio and/or the signal to noise plus distortion ratio.

In accordance with still further aspects of the disclosure, the pump system includes an analog to digital converter that converts the time continuous signal to a digital signal. A sample mode selector is connected to the analog to digital converter for selecting one of a synchronous sample mode or an asynchronous sample mode. If the asynchronous sample mode is set, the sampling rate of the analog to digital converter is set by a reference clock, and if the synchronous sample mode is set, the sampling rate of the analog to digital converter is set according to the frequency of the time continuous signal.

BRIEF DESCRIPTION OF THE DRAWINGS

Other objects and advantages of the invention will become apparent upon reading the following detailed description and upon reference to the drawings in which:

FIGS. 7A-7E illustrate additional aspects of physiologic control modes in accordance with aspects of the present invention.

Figure 1:
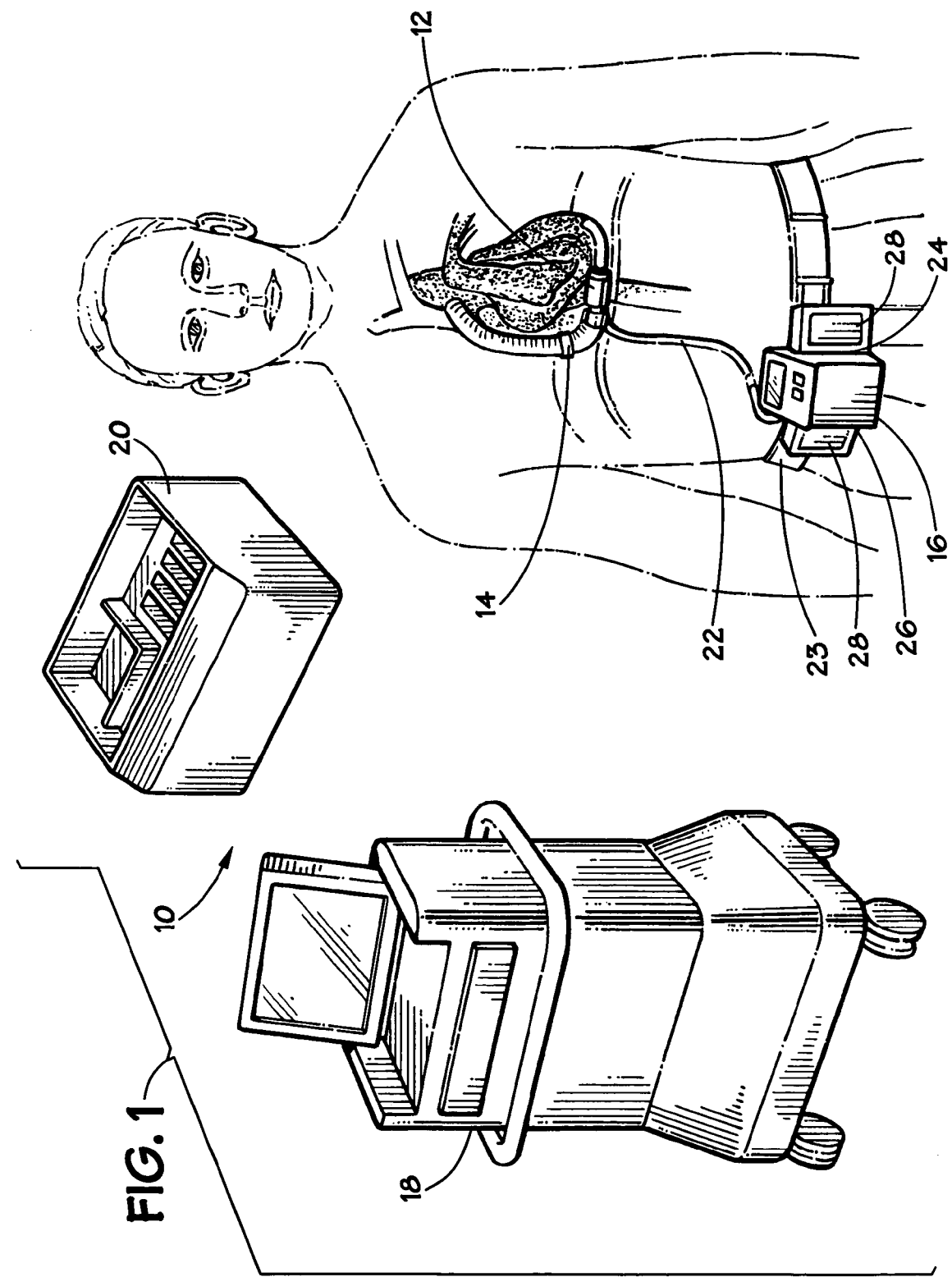
FIG. 1 schematically illustrates various components of an implantable pump system in accordance with embodiments of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Turning to the figures, FIG. 1 illustrates a ventricle assist device (VAD) system 10 such as disclosed in U.S. Pat. No. 6,183,412, which is commonly assigned and incorporated herein by reference in its entirety. The VAD system 10 includes components designed for implantation within a human body and components external to the body. Implantable components include a rotary pump 12 and a flow sensor 14. The external components include a portable controller module 16, a clinical data acquisition system (CDAS) 18, and a patient home support system (PHSS) 20. The implanted components are connected to the controller module 16 via a percutaneous cable 22.

Figure 2:
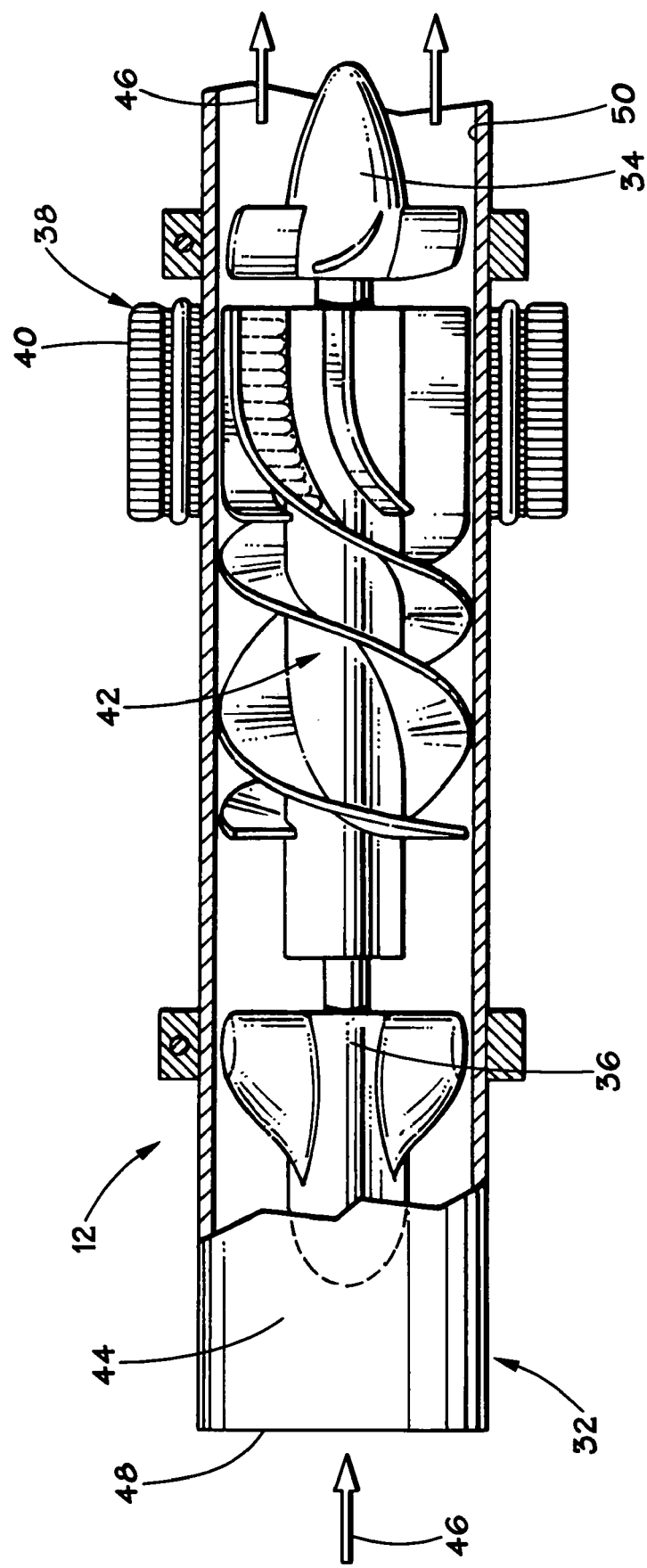
FIG. 2 is a cross-section view of an exemplary implantable pump in accordance with embodiments of the present invention.

The VAD System 10 may incorporate an implantable continuous-flow blood pump, such as the various embodiments of axial flow pumps disclosed in U.S. Pat. No. 5,527,159 or in U.S. Pat. No. 5,947,892, both of which are incorporated herein by reference in their entirety. An example of a blood pump suitable for use in an embodiment of the invention is illustrated in FIG. 2. The exemplary pump 12 includes a pump housing 32, a diffuser 34, a flow straightener 36, and a brushless DC motor 38, which includes a stator 40 and a rotor 42. The housing 32 includes a flow tube 44 having a blood flow path 46 therethrough, a blood inlet 48, and a blood outlet 50.

The stator 40 is attached to the pump housing 32, is preferably located outside the flow tube 44, and has a stator field winding 52 for producing a stator magnetic field. In one embodiment, the stator 40 includes three stator windings and may be three phase "Y" or "Delta" wound. The rotor 42 is located within the flow tube 44 for rotation in response to the stator magnetic field, and includes an inducer 58 and an impeller 60. Excitation current is applied to the stator windings 52 to generate a rotating magnetic field. A plurality of magnets 62 are coupled to the rotor 42. The magnets 62, and thus the rotor 42, follow the rotating magnetic field to produce rotary motion.

Figure 3:
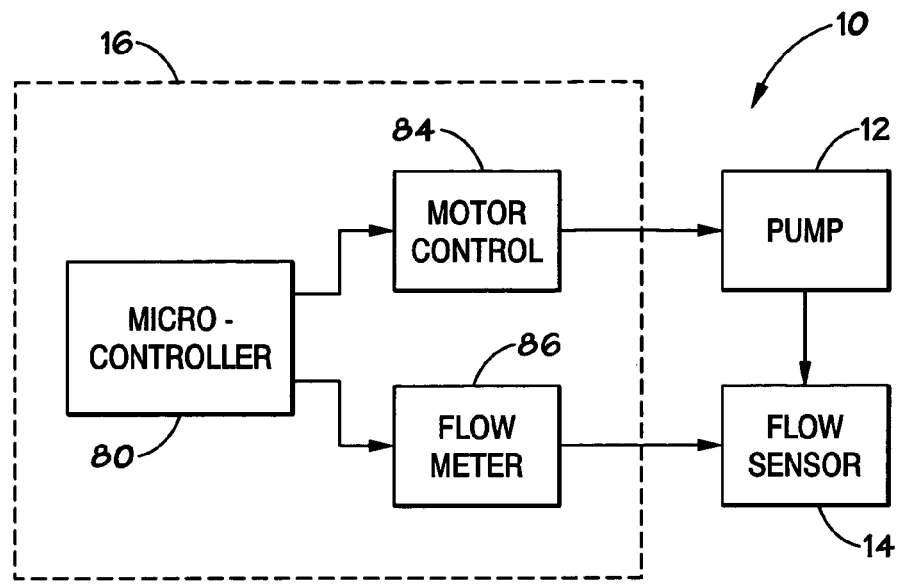
FIG. 3 is a block diagram illustrating aspects of a controller module in accordance with embodiments of the present invention.

FIG. 3 conceptually illustrates aspects of the pump system 10. More specifically, portions of the controller module 16 and the pump 12 are shown. The controller module 16 includes a processor, such as a microcontroller 80, which in one embodiment of the invention is a model PIC16C77 microcontroller manufactured by Microchip Technology. The microcontroller 80 includes a multiple channel analogue to digital (A/D) converter, which receives indications of motor parameters from the motor controller 84. Thus, the controller module 16 may monitor parameters such as instantaneous motor current, the DC component or mean value of the motor current, and motor speed.

The embodiment shown in FIG. 3 further includes an integral flow meter 86. At least one flow sensor 14 is implanted down stream of the pump 12. Alternately, a flow sensor 14 may be integrated with the pump 12. The flow meter 86 is coupled between the implanted flow sensor 14 and the microcontroller 80. The flow meter 86 receives data from the flow sensor 14 and outputs flow rate data to the microcontroller 80, allowing the system to monitor instantaneous flow rate.

Since the implanted flow sensor 14 is coupled to the flow meter 86 of the controller module 16, a true measure of system performance (flow rate) is available for analysis, in addition to pump parameters such as motor speed and current (power). Further, since the flow meter 86 is an integral component of the controller module 16, flow rate may be displayed on the controller module display and flow rate data may be saved in the controller module memory.

In exemplary embodiments of the invention, the motor controller 84 comprises a MicroLinear ML4425 Motor Controller. The operation of the brushless DC motor 38 of the present invention requires that current be applied in a proper sequence to the stator windings 52 to create the rotating field. Two stator windings 52 have current applied to them at any one time, and by sequencing the current on and off to the respective stator windings 52, the rotating magnetic field is produced. In an embodiment of the invention, the motor controller 84 senses back electro motive force (EMF) voltage from the motor windings 52 to determine the proper commutation phase sequence using phase lock loop (PLL) techniques. Whenever a conductor, such as a stator winding 52, is "cut" by moving magnetic lines of force, such as are generated by the magnets 62 of the brushless DC motor 38, a voltage is induced. The voltage will increase with rotor speed 42. It is possible to sense this voltage in one of the three stator windings 52 because only two of the motor's windings 52 are activated at any one time, to determine the rotor 42 position.

An alternative method of detecting the rotor 42 position relative to the stator 40 for providing the proper stator winding 52 excitation current sequence is to use a position sensor, such as a Hall Effect sensor or optical encoder. Implementing aspects of the present invention using a motor with rotor position sensors, rather than a sensorless motor, would be a routine undertaking for one skilled in the art having the benefit of this disclosure. However, adding additional components, such as Hall effect sensors, requires additional space, which is limited in any implanted device application. Further, using a position detection device adds sources of system failures.

The motor controller 84 operates to maintain the pump 12 at an essentially constant speed regardless of the differential pressure across the pump or the flow through the pump. As noted above, the motor controller 84 uses PLL to control the speed of the pump motor 38 (commutation control). An additional analog closed-loop control circuit controls the onboard pulse width modulator (PWM) to maintain a desired speed setting. Both control-loops work in unison to maintain proper speed control.

The motor controller 84 forms a PLL with a voltage-controlled oscillator (VCO), back-EMF sampling error amplifier, loop-filter, sequencer, and output driver. The motor controller 84 samples the instantaneous motor phase that is not energized to determine whether to increase or decrease the commutator (VCO) frequency. The VCO generates an output frequency (commutation rate) proportional to input voltage. A late commutation causes the error amplifier to charge the loop filter, increasing the VCO input while early commutation causes the error amplifier to discharge the loop filter, decreasing the VCO input. The PWM loop, operating at approximately 25 kHz in exemplary embodiments, effectively maintains the desired speed setting once the PLL has reached steady-state (the desired target speed). Constant speed control of the three-phase pump motor, under varying or pulsatile load conditions, is achieved by varying the amount of current delivered to the stator windings proportionally to the motor's load.

The commutation and PWM loops have, because of their associated filter networks, individual frequency and time domain responses associated with them. The frequency range over which the loop system will follow changes in the input frequency is called the lock-in range. The frequency range over which the loop acquires phase-lock is the capture range, and is, in this system, less than the lock-in range.

The dynamic characteristics of the phase-locked loop, and thus the way the pump motor responds to changes in load, are controlled primarily by the loop filter. The filter network included in the PLL serves two major functions. First, it removes any noise and high-frequency components from the error amplifer's output providing an average (dc) voltage to be fed to the VCO's input, and it is the primary element that determines the dynamic performance of the loop including capture (pull-in) range, lock-in range, bandwidth, and transient response.

Once the loop is phase-locked, the filter limits the speed of the loop to track changes in the input frequency (motor speed). In addition, the loop filter provides a "fly-wheel" effect, ensuring a rapid recapture of the signal if the system is thrown out of lock by a noise transient.

Variations in differential pressure across the pump 12 will impart instantaneous changes in pump's load, which will further result in an instantaneous change in the speed of the pump motor 38. The motor controller 84 will sense this change in speed through its back-EMF sampler and attempt to speed up or slow down the pump motor 38, such that the preset speed is maintained. This instantaneous load change and corresponding correction performed by the motor controller 84 will result in a corresponding variation in the pump's current (power), speed and flow waveforms. An instantaneous increase in the pump's load will cause an instantaneous decrease in pump speed and thus an instantaneous increase in pump current (power) and decrease in flow rate. Conversely, an instantaneous decrease in the pump's load will cause an instantaneous increase in pump speed and thus an instantaneous decrease in pump current (power) and increase in flow rate.

Therefore, the pump's current (and therefore power), speed, and flow waveforms correlate well with changes in the pump's load. These waveforms may be used to calculate the patient's heart rate, instantaneous and mean blood flow rate, regurgitant flow, instantaneous and mean power consumption, the pump's efficiency (e.g. dQ/dn or dQ/dP), etc. These waveforms also indicate when the pump's speed is set too high and the ventricle begins to collapse. This condition exists when the flow and/or current waveforms are highly-asymmetric and/or their peaks appear to contain multiple ripples or are flattened (clipped). Additionally, waveforms with short negative rise-times (attack) followed by slower positive exponential fall-times (decay) indicate suction.

The aforementioned signals, current (power), speed, and flow, are time-continuous band-limited signals. The current signal is a composite signal containing the motor controller's PWM frequency, the patients heart rate (assuming there is a heart rate), and other frequencies relating to certain physiologic responses within the patient's cardiovascular system (e.g. respiratory rate, valve openings and closures, changes in systemic resistance, etc.). The pulse-width modulation frequency typically is approximately 25 kHz and the patient's pulse rate is approximately 0.7 Hz to 4.0 Hz (i.e. 40 BPM (beats per minute) to 240 BPM). A two-pole maximally flat low-pass Butterworth Filter ($f_c$=250 Hz) within the controller module 16 may be used to limit the bandwidth of this signal.

The power signal is the product of the pump motor current and pump motor voltage (a constant scalar) and is therefore a composite signal which, like the current, contains the motor controller's pulse-width modulation (PWW frequency, the patient's heart rate (assuming there is a pulse rate), and other frequencies relating to certain physiologic responses within the patient's cardiovascular system (e.g. respiratory rate, valve openings and closures, changes in systemic resistance, etc.). The pulse-width modulation frequency is approximately 25 kHz and the patient's pulse rate is approximately 0.7 Hz to 4.0 Hz (i.e. 40 BPM to 240 BPM).

The speed signal typically contains the heart rate of the patient (assuming there is a native heart rate) as the dominant frequency along with other frequencies related to certain physiologic responses within the patient's cardiovascular system (e.g. respiratory rate, valve openings and closures, changes in systemic pressure, etc.). The angular momentum of the rotor impeller and viscosity of the blood dampen abrupt changes in speed and thus the bandwidth of this signal is typically below 30 Hz.

The flow signal typically contains the heart rate of the patient (assuming there is a native heart rate) as the dominant frequency along with other frequencies related to certain physiologic responses within the patient's cardiovascular system (e.g. respiratory rate, valve openings and closures, changes in systemic pressure, etc.). A two-pole maximally-flat Butterworth Filter ($f_c=30$ Hz) within the controller module 16 limits the bandwidth of this signal.

Variations in the flow, speed, current, and power waveforms in the time domain will result in corresponding variations in their frequency domain representations. The frequency domain representations for these signals may be obtained through the application of the Discrete Fourier Transform (DFT) or the Fast Fourier Transform (FFT), though the FFT is more efficient computationally than is the DFT and is generally more easily realized in hardware and/or software. Continuous conversion of these time continuous physiologic signals from the time domain to the frequency domain provides real-time spectral content information about these signals.

Figure 4:
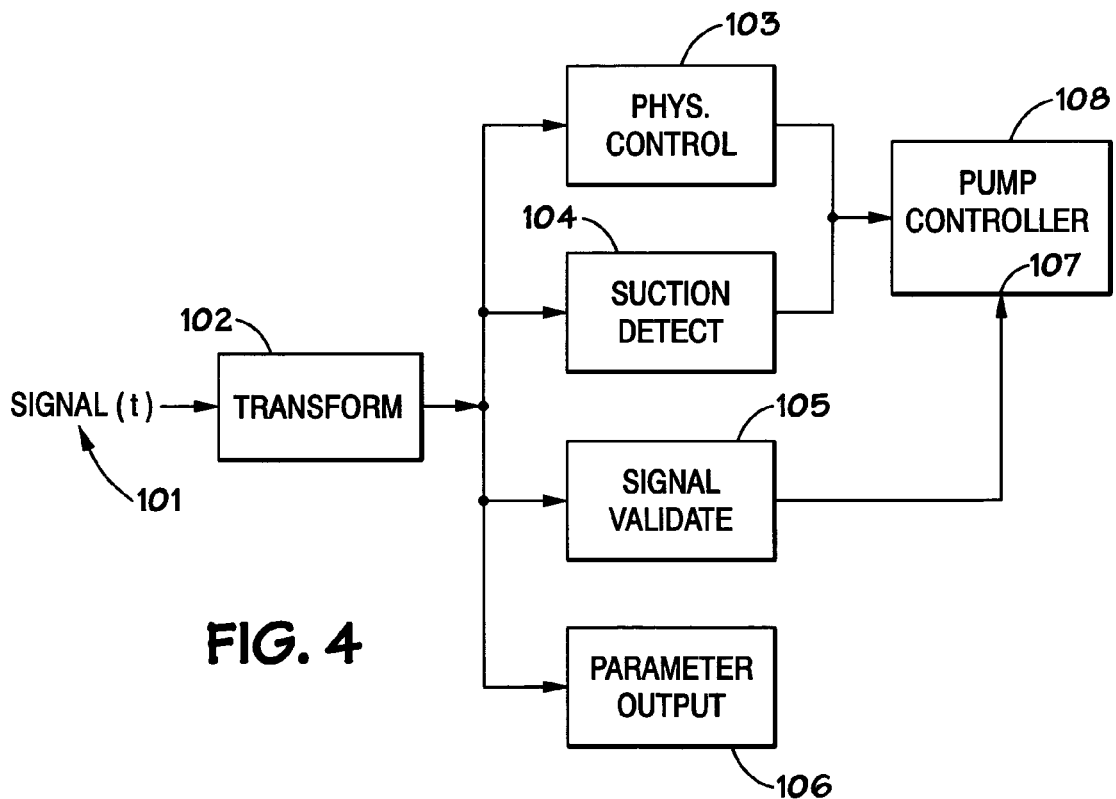
FIG. 4 is a block diagram conceptually illustrating a pump control system in accordance with embodiments of the present invention.

In accordance with exemplary embodiments of the present invention, methods and mechanisms are presented, through use of the DFT and/or FFT, to provide simultaneous physiologic control of the pump 12, signal validation and ventricular suction detection in the frequency domain using a single data set. FIG. 4 is a block diagram conceptually illustrating an integrated pump control system 100 in accordance with aspects of the present invention.

The control system 100 may be implemented in software, hardware, or a combination thereof. Software implementations include using the microcontroller 80 provided in the controller module 16. Alternatively, a stand-alone microcontroller or a digital signal processor ("DSP"), for example, may be used. Exemplary hardware implementations may include a field programmable gate array ("FPGA"), a complex programmable logic device ("CPLD"), application specific integrated circuits ("ASIC"), discrete analog and/or digital components, etc.

A time continuous physiologic signal 101 (flow rate, current, etc.) is received from the pump 12 and/or flow sensor 14. The time continuous signal 101 is then transformed to the frequency domain in block 102. The frequency domain representation 102 of the sampled signal 101 is then used for simultaneous physiologic control 103 of the pump 12 and suction detection 104.

Figure 5:
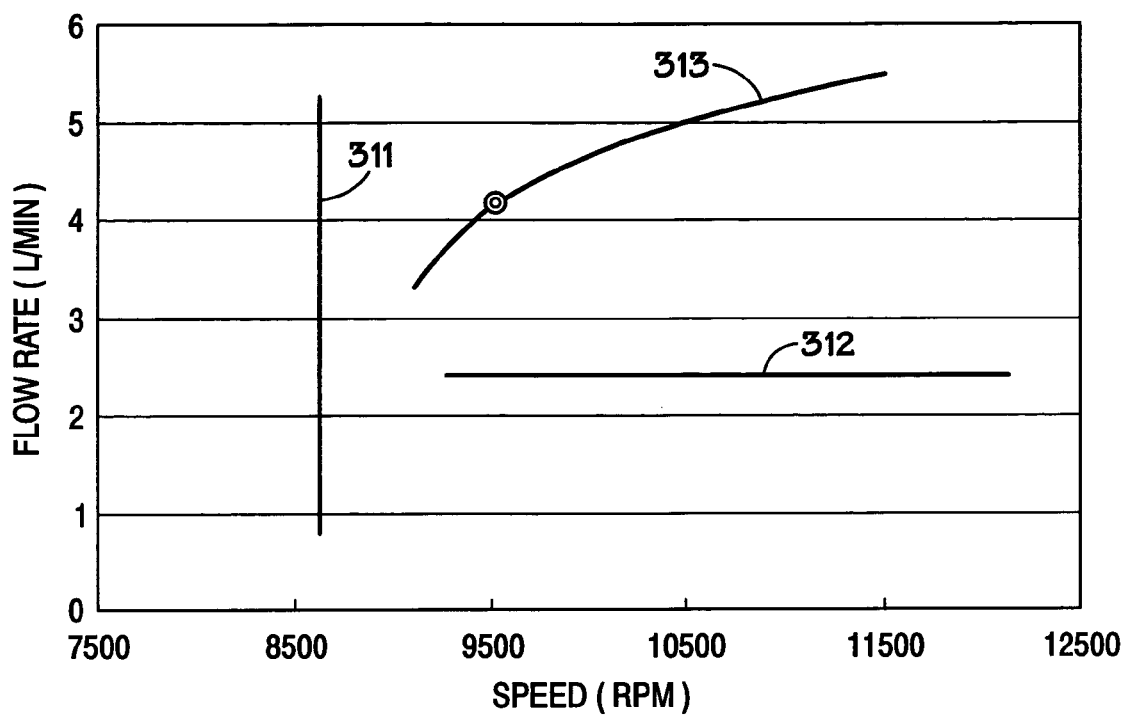
FIG. 5 illustrates exemplary physiologic control modes in accordance with aspects of the present invention.

FIG. 5A illustrates three exemplary physiologic control modes 103 in accordance with aspects of the present invention that employ suction detection and physiologic "triggers": "constant speed" 311, "constant flow" 312, and "maximize, or maximal, flow" 313. These control modes are shown via a plot of flow rate vs. pump speed. In the constant speed mode 311, the pump speed remains constant with changes in flow rate and in the constant flow mode 312, the flow rate remains constant as the speed varies. The constant speed mode is suitable, for example, intraoperatively, while weaning the patient off cardiopulmonary bypass, following surgery, and when the patient is discharged from the hospital. As noted above, the pump is operated at a fixed, predetermined speed. The speed may be optionally adjusted in response to suction events—i.e., the pump speed may be reduced in response to detected suction events. The constant flow mode is suitable, for example, for patients in intensive care (ICU), recovery or during weaning from bypass.

The maximize, or maximal, flow mode 313 is suitable, for example, during recovery or during exercise. With the maximize flow mode 313, the pump speed is periodically increased until a "diminishing returns" point is reached, and/or until another predetermined limit is reached (i.e. maximum power, maximum pump speed, etc.). In other words, the controller increases pump speed to a point at which an increase in pump speed no longer produces a corresponding increase in flow or a corresponding decrease in peak-to-peak amplitude. The maximize flow mode may be manually enabled by the patient, for instance, via a push button at the start of exercise, or it may be automatically triggered in response to a predetermined parameter.

Figure 6:
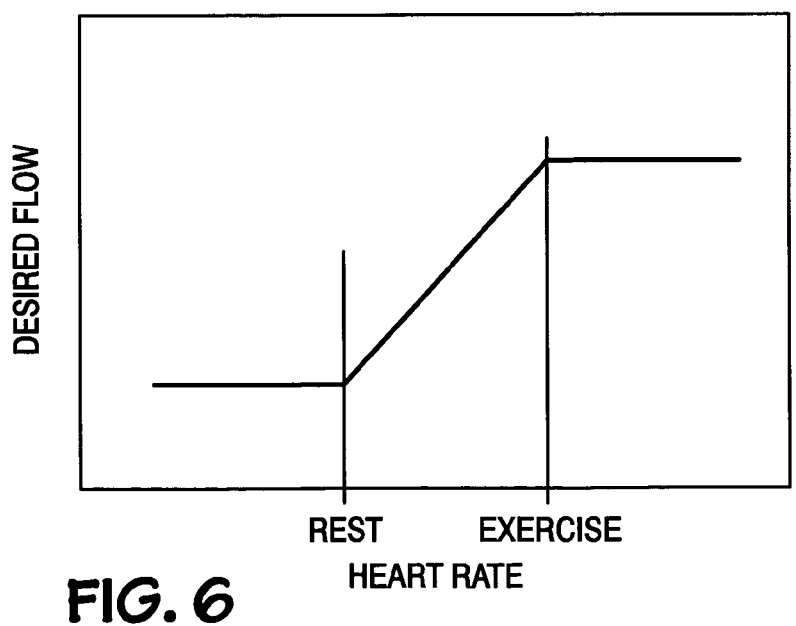
FIG. 6 is a graph showing another control mode in accordance with aspects of the present invention.

FIG. 6 shows a control mode in which the desired flow rate is generally proportional to a linear interpolation of heart rate. Desired rest and exercise flow rates are established, and in the illustrated mode, the desired flow rates do not go below or above these rates, respectively, regardless of the heart rate. Between the rest and exercise heart rates, the desired flow rate varies with heart rate.

FIG. 7 provides additional aspects of the constant speed, constant flow and maximize flow, as well as a "constant peak-to-peak amplitude" mode. In some implementations, the physician may select which control mode is the most appropriate for the patient. The means to enable a true "physiologic" response is via a trigger—for example, diastolic flow or heart rate, or a combination of the two, as identified in the incorporated applications. Alternatively, a manual trigger, such as an "exercise" button on the controller 16 may be used. The physician may selectively enable or disable the exercise button or the automatic triggers and may selectively decide if flow will be maximized by "diminishing returns" (change in flow for a given change in speed) or maximized by "minimal peak-to-peak amplitude" (the flow pulsatility, or peak-to-peak amplitude, decreases as pump speed is increased)

If the desired flow for the patient cannot be achieved (e.g. a boundary condition is reached such as maximum speed, maximum power, or minimum pulsatility), then pump speed is not adjusted further. In other implementations, the control mode may be changed and the pump speed is reduced to achieve a desired peak-to-peak amplitude. In the control modes shown in FIG. 7, suction detection is either enabled or disabled but the corresponding alarm remains active. In other embodiments, varying levels of "ventricular unloading" are employed, assuming that the risk for suction is greatest with lower flow pulsatility.

Control parameters for each of the control modes are summarized and described in FIG. 7. For example, in the constant speed control mode shown in FIG. 7A, a clinician enters values for parameters shown in bold—the desired pump speed and the minimum flow rate. The values shown in regular type (not in bold) are default values that can be manually changed by the clinician. Additionally, the clinician enables or disables the "suction detection" and "suction detection response" parameters. If the suction response is enabled, upon detection of suction, the controller 16 activates a diagnostic alarm and reduces the pump speed by a predetermined amount and rate until suction disappears. For a suction-triggered speed reduction, the controller is programmed to wait a predetermined amount of time, then increase the speed by a predetermined amount and rate until the nominal speed is again achieved. If suction is detected again and the speed is reduced in response thereto (prior to achieving the nominal speed), the controller repeats the delay and subsequent speed increases. If suction is detected a third time with a corresponding speed reduction prior to achieving the nominal speed, the speed increase process repeats with a slower time period. A tone or other audible or visual signal is activated when the nominal speed is achieved. If the suction response is disabled, the diagnostic alarm is activated but no additional automatic responses are executed. If either the minimum speed or minimum flow is reached, the controller activates a diagnostic alarm and the speed is not reduced any further.

If the signal from the flow meter 86 (or Flow Sensor Board, FSB) is not received or is corrupted, for example, a "bad flow signal" flag is set. In response to the detection of a poor flow signal, the controller 16 activates a diagnostic alarm, the speed setting is not changed, and the FSB is reinitialized. If the flow signal is still considered unusable or invalid, the controller 16 reinitializes the FSB periodically and suppresses the low flow alarm. If the flow signal returns (i.e. considered to be valid), the controller 16 reverts back to the desired control mode, if the desired mode is other than the constant speed mode. Similarly, if a poor quality flow signal is received, the controller 16 activates a diagnostic alarm, maintains the current speed setting and suppresses the low flow alarm. If the pump reaches the maximum power level, a diagnostic alarm is activated.

In the constant flow mode shown in FIG. 7B, the desired flow rate is entered, and the maximum power and minimum flow parameters may be calculated based on the desired flow rate from the characteristic flow-pressure curves of the pump. The remaining parameters are default values that may be manually changed by the clinician. Upon detection of suction, the controller 16 activates a diagnostic alarm and reduces speed by a predetermined amount and rate until the suction disappears. If the minimum speed or minimum flow level is reached, the controller 16 activates a diagnostic alarm and does not reduce the speed any further.

For a suction-triggered speed reduction, the controller 16 is programmed to wait a predetermined amount of time, then increase the speed by a predetermined amount and rate until the nominal flow is again achieved. If suction is detected again, and the speed is reduced in response thereto (prior to achieving the nominal flow), the controller 16 repeats the delay and subsequent speed increases. If suction is detected a third time, with a corresponding speed reduction prior to achieving the nominal flow, the speed increase process repeats. The system may also be programmed to adaptively respond to suction events. The suction indices described herein provide continuous real-time indications of the degree of suction (i.e. 0% to 100%) and thus, the higher the index value, the greater the probability of suction. Therefore, the system may be designed to reduce the pump's speed by an amount proportional to the degree of suction (i.e. a higher suction index yields a greater speed reduction than a lower suction index). A tone or other signal is activated when the nominal flow is achieved. If a bad flow signal or poor flow signal quality is received, the controller activates a diagnostic alarm and reverts to the constant speed control mode, with the speed set at "FSB fail speed"—typically 9000 RPM or the fail-safe speed, 8500 RPM. If the maximum power threshold setting is reached, the controller 16 activates a diagnostic alarm and the speed is not allowed to increase further. If the maximum speed setting is reached, a diagnostic alarm is activated and the speed is not increased above the maximum speed value.

In the constant peak-to-peak amplitude mode shown in FIG. 7C, the minimum flow parameter is entered and control is based on the peak-to-peak amplitude ("P2P") of the flow signal. The remaining parameter values are defaults that can be manually changed by the clinician. If suction is detected the controller 16 activates a diagnostic alarm and reduces speed by a predetermined amount and rate until the desired peak-to-peak amplitude is achieved. If the minimum speed or minimum flow setting is reached, the controller 16 activates a diagnostic alarm and does not reduce speed any further.

In the event of a suction triggered speed reduction, the controller 16 waits a predetermined amount of time, then increases speed by a predetermined amount and rate until the nominal peak-to-peak amplitude value is achieved. If, prior to reaching the nominal peak-to-peak amplitude, a suction triggered speed reduction occurs again, the speed increase is repeated after a predetermined time period. If a suction triggered speed reduction occurs a third time, the speed increase is repeated at a slower repetition rate. The controller 16 activates a tone or other signal when the nominal peak-to-peak amplitude is achieved. If a "bad" flow signal or poor quality flow signal quality is received, the controller 16 activates a diagnostic alarm and reverts back to the constant speed control mode, with the speed set at the FSB fail speed. If the maximum speed or power threshold levels are reached, the controller activates a diagnostic alarm and the speed is not increased further.

FIGS. 7D and 7E summarize the maximize flow algorithms based on peak-to-peak amplitude (pulsatility) or diminishing returns (change in flow vs. change in pump speed). The maximize flow mode is either enabled or disabled via settings on the CDAS 18. If the maximize flow mode is enabled, then either the peak-to-peak amplitude (P2P) or point of diminishing returns (dQ/dn) algorithm must be selected. Once the maximize flow mode is selected, the various triggers (e.g. diastolic flow, heart rate or exercise, for example) are individually enabled or disabled. In the illustrated embodiments, the maximize flow modes do not "branch" to any other modes; they may only return to the original control mode.

In the "maximize flow" control mode, based on peak-to-peak amplitude, the controller varies speed to maintain constant peak-to-peak amplitude of the flow signal. The peak-to-peak amplitude value may be dependent on the desired degree of ventricular unloading (for example, low, medium, high). If excess suction is detected, the controller activates a diagnostic alarm, reduces speed by some predetermined rate (200 RPM in one implementation) per second until suction disappears, waits 15 seconds, then attempts to servo to peak-to-peak amplitude.

The maximize flow mode based on diminishing returns is summarized in FIG. 7E. Speed is increased a predetermined amount and rate until the desired dQ/dn is achieved. Periodically, speed is increased to check dQ/dn. The speed is then decreased, and if the dQ/dn does not vary, the controller continues to decrease the speed. In other words, the speed is always increased once, then decreased twice, then the controller waits a predetermined amount of time. If excess suction is detected, the controller 16 activates a diagnostic alarm and reduces speed at a predetermined rate until the suction disappears. The controller then waits a predetermined amount of time, and then repeats the dQ/dn routine.

With either the peak-to-peak amplitude or diminishing return modes, if the minimum speed setting is reached, a diagnostic alarm is activated and the speed is not reduced further (i.e. constrained in hardware for safety). If the minimum flow value is reached, the controller 16 activates a diagnostic alarm, the speed is not reduced further, and the controller reverts back to original control mode. If the maximum speed or power value is reached, the controller 16 activates a diagnostic alarm and does not increase the speed any further. If a bad flow signal is received, the controller 16 activates a diagnostic alarm and reverts to the original control mode. The "baseline" flow is the mean flow prior to entering the maximize flow control mode. If the "Allow Flow Below Baseline" is enabled, the minimum flow threshold is a percentage of the baseline flow (baseline flow*predetermined percentage of baseline). The default setting for flow is "Not allowed below baseline".

In exemplary embodiments, the minimum speed limit is 7.5 kRPM, and the maximum speed limit is 12.5 kRPM. The hardware fail-safe speed is 8.5 kRPM. The bad flow signal or poor flow signal quality set speed ("FSB fail speed") is 9.0 kRPM. The controller module 16 indicates which mode is active, and also indicates whether peak-to-peak amplitude or "diminishing returns" is selected for the maximize flow algorithm and which triggers are active. The controller 16 further includes an "Exercise" button that is illuminated anytime the maximize flow algorithm is activated. In certain embodiments, the controller 16 is programmed such that the patient can defeat the maximize flow algorithm by holding the Exercise Button for a predetermined length of time, which also functions to defeat the automatic triggers for some predetermined time period.

In accordance with embodiments of the invention, the excess suction operation 104 uses spectral analysis equations to process the frequency domain data representation and generate suction probability indexes. These spectral analysis equations include analyses based on harmonic distortion, total spectral distortion (harmonic distortion and noise), sub-fundamental distortion (distortion below the fundamental frequency), super-fundamental distortion (distortion above the fundamental frequency), the ratio of the super-fundamental distortion to the sub-fundamental distortion, super-physiologic distortion (distortion at frequencies above the assumed maximum physiologic fundamental frequency—typically 4 Hz or 240 BPM), and the spectral dispersion or "width" of the resulting flow(f) waveform. These spectral analysis techniques are addressed in detail as follows.

The spectral distortion factor measures the ratio of all energy contributed by all frequencies about the fundamental frequency with respect to the fundamental frequency. A higher distortion ratio indicates a higher probability of suction.

$$\text{Spectral distortion factor} = \frac{\left[\sqrt{\sum_{n=1}^{x} [A[f_{(n \cdot dF)}]]^2 - [A[f_1]]^2}\right] \cdot 100}{|A[f_1]|}$$

wherein n indicates the spectral component's index/position in the resulting array; x is the last index/position in this array; dF represents the frequency resolution/interval of the resulting DFT operation in Hertz; and $f_1$ is the fundamental frequency, the maximum (amplitude) spectral peak in the DFT resultant array. Since the spectral analysis of the flow rate signal pertains to the AC component, and not the mean value or offset, the range of interest does not include n=0 because the mean flow rate or DC component of the flow(f) waveform occurs at n=0. This is true for all of the frequency domain suction probability indices contained herein.

The harmonic distortion factor measures the ratio of energy contributed by all harmonics about the fundamental frequency with respect to the fundamental frequency.

$$\text{Harmonic distortion factor} = \frac{\left[\sqrt{\sum_{n=2}^{x} [A[f_n]]^2}\right] \cdot 100}{|A[f_1]|}$$

wherein n indicates the $n^{th}$ harmonic in the resulting array; x is the highest harmonic in this array; $f_1$ is the fundamental frequency, the maximum (amplitude) spectral peak in the DFT resultant array; and $f_n$ represents integer multiples of the fundamental $f_1$ from n=2 (second harmonic) to x ($x^{th}$ harmonic).

The sub-fundamental distortion factor measures the additive frequency contributions below the fundamental frequency with respect to the fundamental frequency.

$$\text{Sub-fundamental distortion factor} = \frac{\left[\sqrt{\sum_{n=1}^{n(f1)-1} [A[f_{(n \cdot dF)}]]^2}\right] \cdot 100}{|A[f_1]|}$$

wherein n indicates the spectral component's index/position in the resulting array; dF represents the frequency resolution/interval of the resulting DFT operation in Hertz; $f_1$ is the fundamental frequency, the maximum (amplitude) spectral peak in the DFT resultant array; and n(f1) is the index/position of the fundamental.

The super-fundamental distortion factor measures the additive frequency contributions above the fundamental frequency with respect to the fundamental frequency.

$$\text{Super-fundamental distortion factor} = \frac{\left[\sqrt{\sum_{n=n(f1)+1}^{x} [A[f_{(n \cdot dF)}]]^2}\right] \cdot 100}{|A[f_1]|}$$

wherein n indicates the spectral component's index/position in the resulting array; x is the last index/position in this array; dF represents the frequency resolution/interval of the resulting DFT operation in Hertz; $f_1$ is the fundamental frequency, the maximum (amplitude) spectral peak in the DFT resultant array; and n(f1) is the index/position of the fundamental.

The super/sub fundamental distortion factor measures the ratio of additive frequency contributions above the fundamental frequency to the additive frequency contributions below the fundamental frequency.

$$\text{Super/sub fundamental distortion factor} = \frac{\left[\sqrt{\sum_{n=n(f1)+1}^{x} [A[f_{(n \cdot dF)}]]^2}\right] \cdot 100}{\left[\sqrt{\sum_{n=1}^{n(f1)-1} [A[f_{(n \cdot dF)}]]^2}\right]}$$

wherein n indicates the spectral component's index/position in the resulting array; dF represents the frequency resolution/interval of the resulting DFT operation in Hertz; x is the last index/position in this array; and n(f1) is the index/position of the fundamental.

The super physiologic distortion factor measures the additive frequency contributions above the maximum expected physiologic frequency (i.e. 4 Hz=240 BPM) with respect to the fundamental frequency.

$$\text{Super physiologic distortion factor} = \frac{\left[\sqrt{\sum_{n=n(f_h)+1}^{x} [A[f_{(n \cdot dF)}]]^2}\right] \cdot 100}{|A[f_1]|}$$

wherein $f_h$ is a spectral peak at frequency=4 Hz; n indicates the spectral component's index/position in the resulting array; x is the last index/position in this array; dF represents the frequency resolution/interval of the resulting DFT operation in Hertz; $f_1$ is the fundamental frequency, the maximum (amplitude) spectral peak in the DFT resultant array.

In other embodiments, the spread of the waveform is measured. As noted above, it is assumed that a physiologically appropriate waveform in the time domain is quasi-sinusoidal at a single frequency proportional to the patient's native heart rate, and hence, the corresponding physiologically appropriate waveform in the frequency domain will be a singly narrow spectral peak at the same single frequency proportional to the patient's native heart rate. Deviations from this quasi-sinusoidal case may indicate suction as well as other defects.

For example, as the flow(t) waveform becomes more distorted, the flow(f) is waveform will contain additional flow contributions at varying frequencies and will thus begin to "widen". The probability that suction is imminent or present increases proportionally to the width of flow(f). The measure of the width of flow(f) about the fundamental frequency is the square-root of the mean-squared variation about the fundamental frequency. The spectral dispersion factor measures the "width" of the flow(f), current(f), speed(f), and/or power(f) signals:

$$\text{Spread Flow} = \frac{\sqrt{\sum_{n=1}^{N} [A[f_{(n \cdot dF)}] - A[f_1]]^2}}{N}$$

wherein $f_1$ is the fundamental frequency, the maximum (amplitude) spectral peak in the DFT resultant array; dF represents the frequency resolution/interval of the resulting DFT operation in Hertz; n indicates the spectral component's index/position in the resulting array; and N is the last index/position in this array. Since the analysis of spread flow is concerned with the wave shape, and not the offset, the range of interest does not include n=0 because the mean flow rate or DC component of the flow(f) waveform occurs at n=0.

Figure 8:
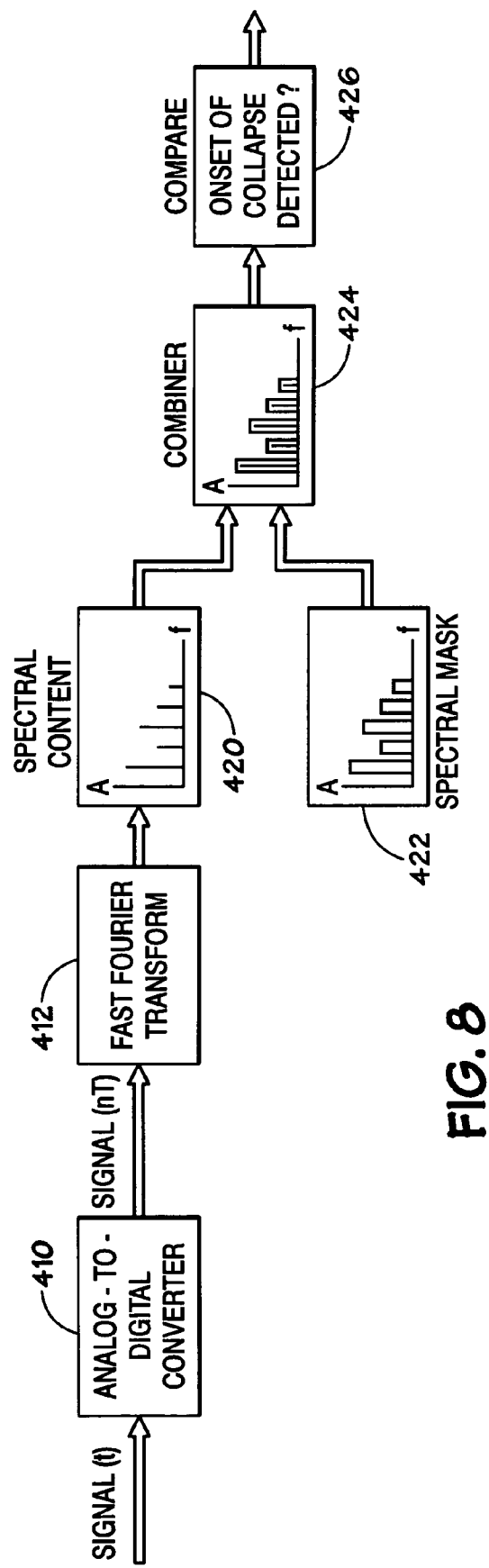
FIGS. 8 and 9 are block diagrams conceptually illustrating methods of detecting ventricle collapse in accordance with embodiments of the present invention.
Figure 9:
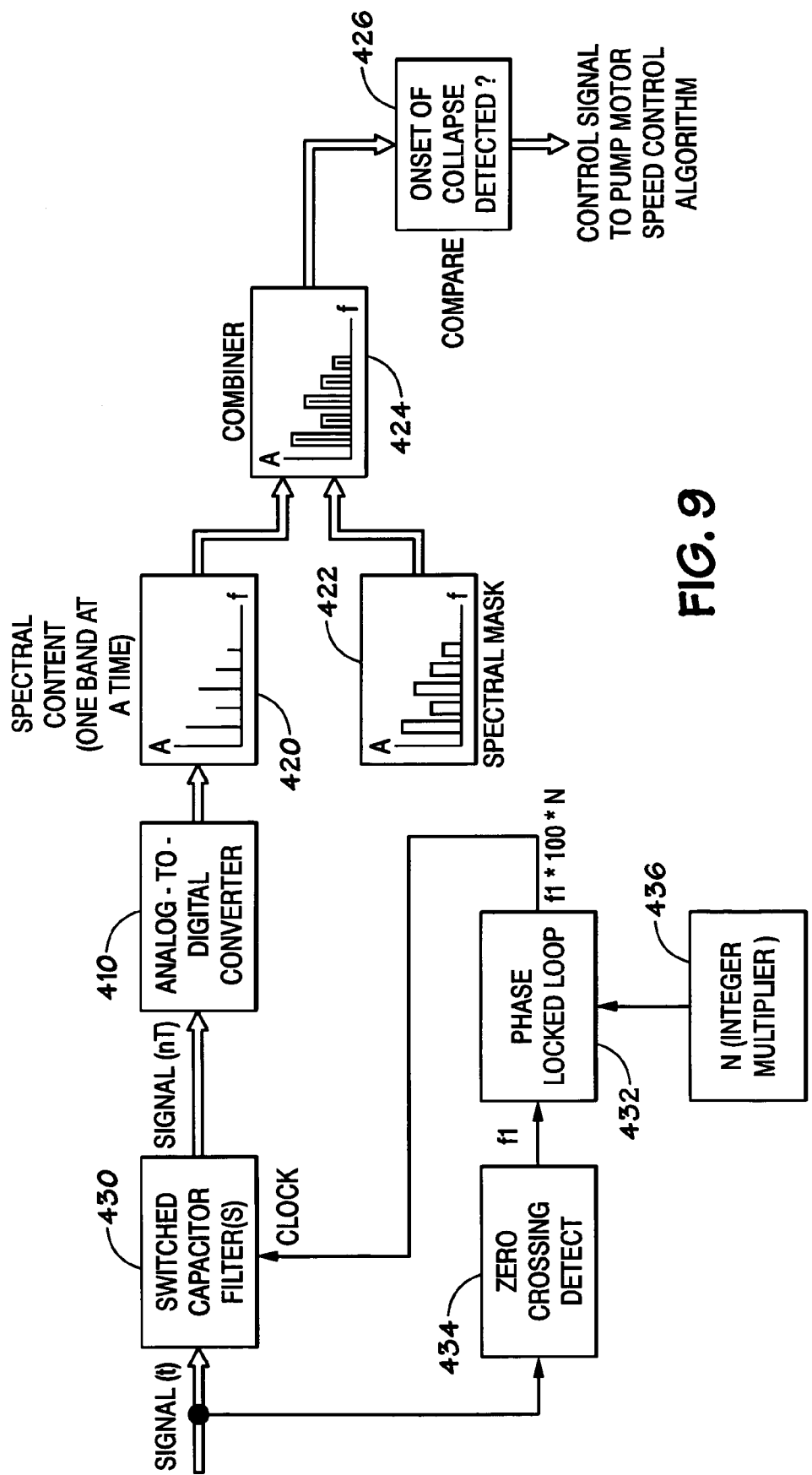

Some alternatives to applying the spectral content of the measured signal to spectral analysis equations are shown in FIGS. 8 and 9, where the real time spectral content measured signal is compared to a predetermined spectral mask. In the embodiment shown in FIG. 8, the spectral content 420 generated by the DFT 412 is compared to a predetermined spectral mask 422 in a combiner block 424. In block 426, the presence of suction is determined based on the comparison. The signals whose spectral components fall within the mask indicate suction and, conversely, signals whose spectral components fall outside the mask indicate normal flow.

In the embodiment shown in FIG. 9, the time domain responses are converted to frequency domain through the application of a synchronous switched-capacitor filter 430. In this exemplary embodiment, the frequency response of the filter 430 is controlled by a clock source one hundred times the desired pass-band frequency. A phase-locked loop 432 generates this clocking signal to the filter 430 by receiving the output from a zero crossing detector 434 and multiplying the incoming fundamental frequency by an integer multiplier 436, the value of which is selected by a digital input element such as a microcontroller. Incrementing the integer multiplier will cause the synchronous filter to "track" the incoming signal and output the spectral amplitude of the fundamental frequency, first harmonic, second harmonic, etc. The sum of the individual spectral amplitudes results in a frequency-domain representation of the time-domain signals.

As in the embodiment illustrated in FIG. 8, a comparison may then be made between the real-time spectral content 420 of these signals and the predetermined spectral mask 422. Signals whose spectral components fall within the mask indicate suction and, conversely, signals whose spectral components fall outside the mask indicate normal flow.

Additionally, the frequency domain representation 102 may be used to validate the integrity of the sampled signal 101. The signal validation process 105 may provide an output to an "enable" setting 107 of the pump control process 108. Still further, real-time extraction of parametric data, such as the patient's heart rate, respiratory rate and pump flow information may be derived from the frequency domain representation 102 and output to a user interface display 106.

Figure 10:
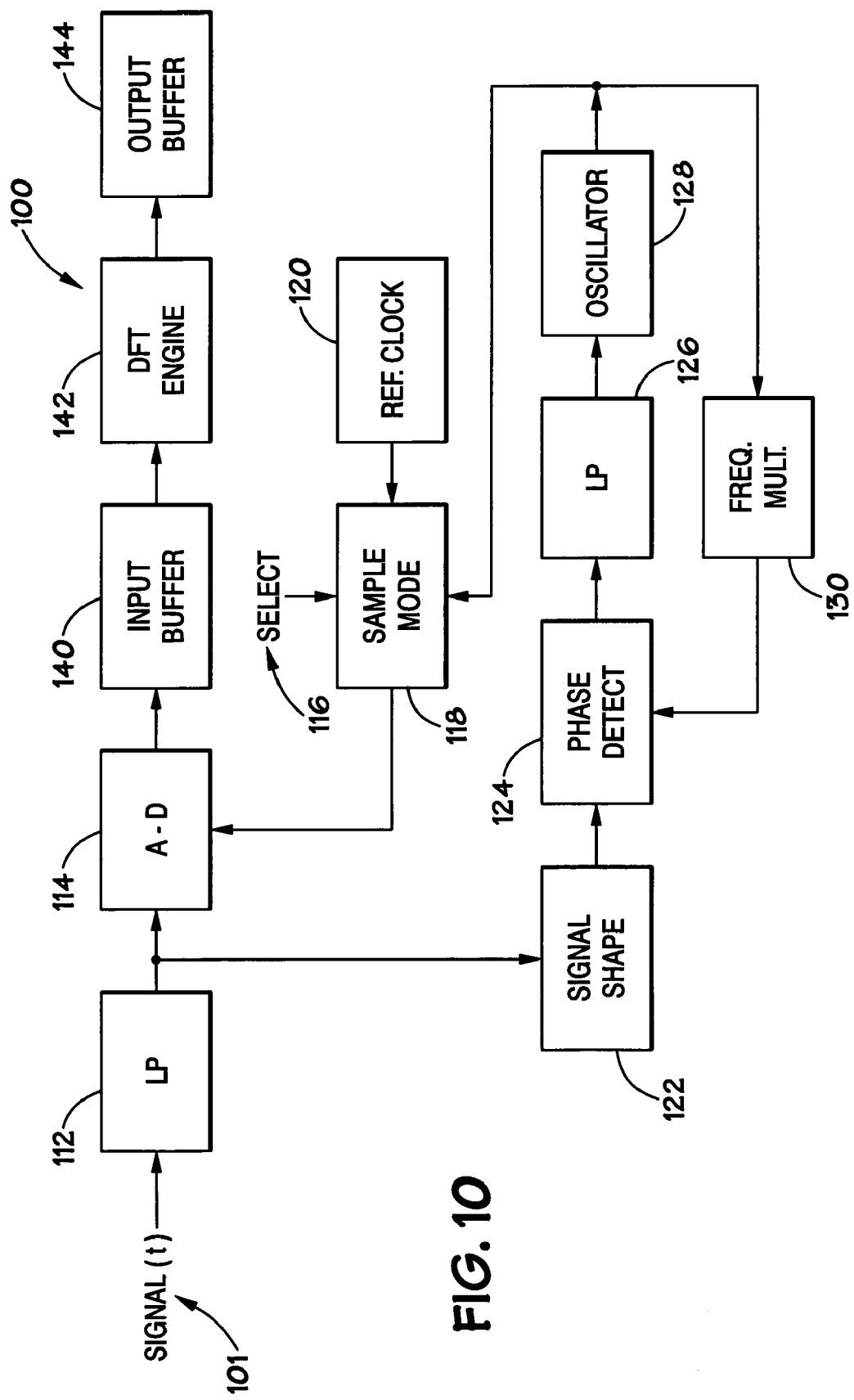
FIG. 10 is a block diagram illustrating further aspects of the exemplary pump control system shown in FIG. 4.

FIG. 10 is a block diagram illustrating further aspects of the pump control system 100 in accordance with an exemplary embodiment of the present invention. The time continuous physiologic signal 101 is restricted below the Nyquist frequency using a low pass antialiasing filter 112. An analog-to-digital converter 114, which may be clocked asynchronously or synchronously based on a mode select input 116 to a sampling mode selector 118, is then used to convert the signals into digital values.

If the asynchronous sampling mode is selected, a fixed timebase reference clock 120 provides the sampling timing source. If the synchronous sampling is selected, a PLL is used to synchronously sample the applied signal 101. After filtering, the applied signal 101 is sent to a signal shaper 122 and a phase detector 124, and the resultant signal is low-pass filtered 126 and provided to a voltage controlled oscillator 128. The synchronous sampling rate is set by a frequency multiplier 130, based on an integer multiple M of the fundamental frequency of the applied signal 101. For example, if M=100, the applied signal 101 will be sampled at a rate proportional to 100 times the fundamental frequency of the applied signal 101. Synchronous sampling, although more complex to implement, minimizes spectral leakage from occurring in the DFT's output array, and enables a more accurate measure of frequency/amplitude information near the fundamental.

The digital signals from the analog-to-digital converter 114 are stored into an input memory buffer 140 of length N for processing by the DFT engine 142. The size of the input memory buffer 140 is governed by the number of points N to be processed by the DFT 142, the amplitude resolution of the samples, the system's sampling rate, and the desired DFT output frequency resolution. An output memory buffer 144 contains half as many points as that of the input memory buffer 140 (N/2) and is used to store the array resulting from the DFT 140, containing the single-sided spectrum of the transformed signal.

Figure 11:
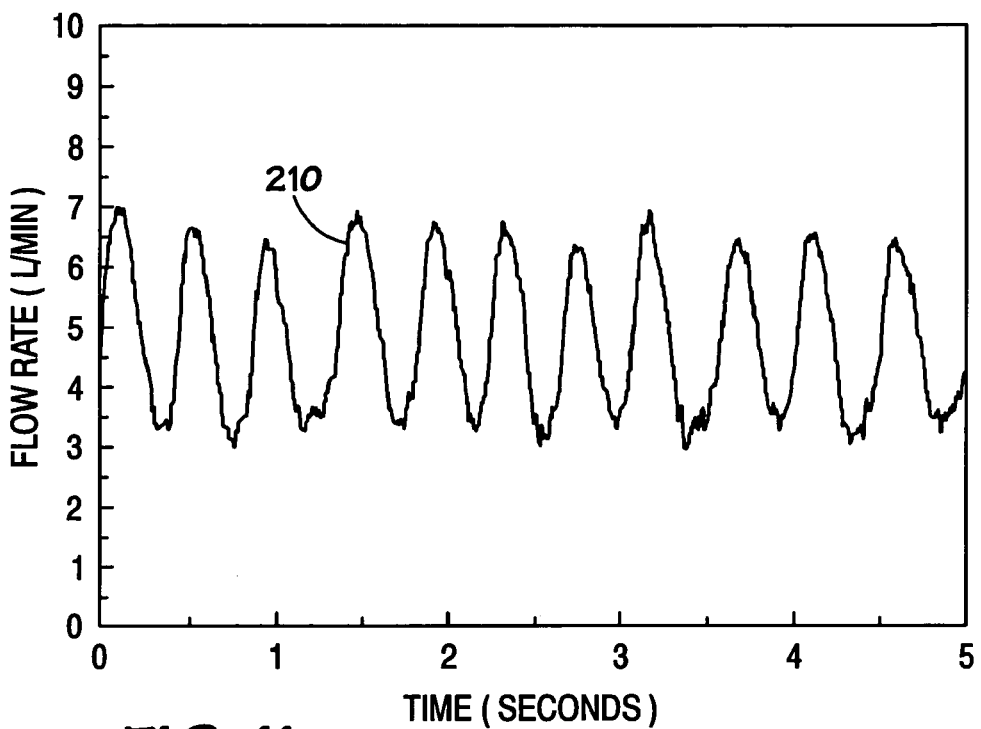
FIGS. 11 and 12 illustrate a "normal" flow waveform (no excessive suction) in the time and frequency domains, respectively.
Figure 12:
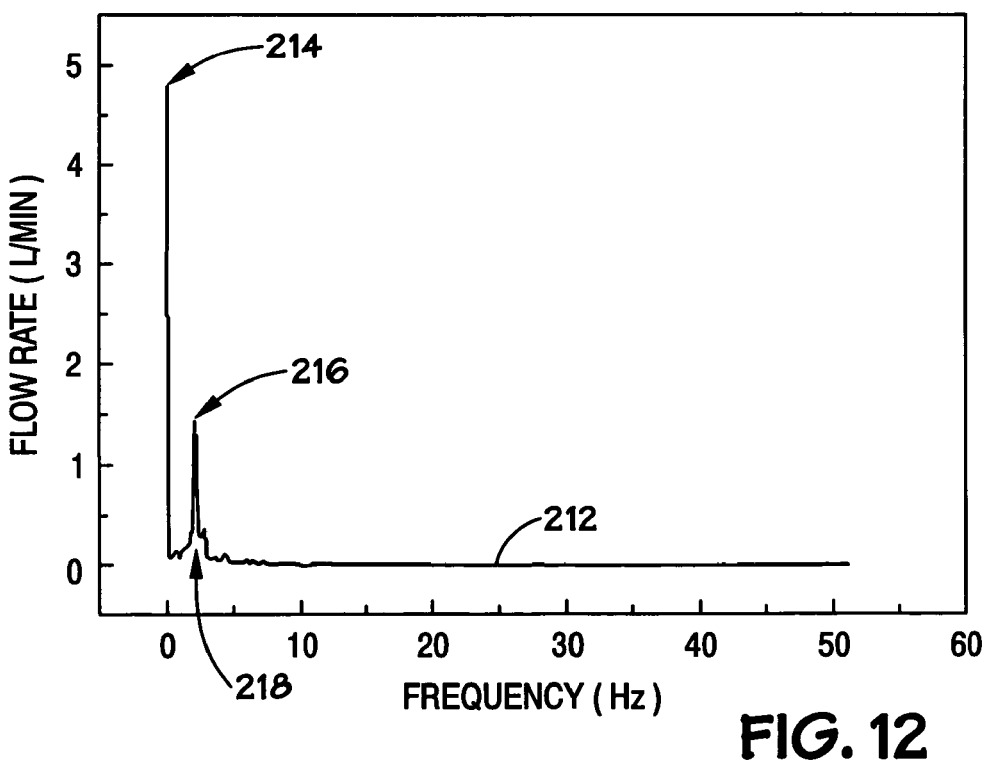

A "normal" flow waveform (no excessive suction) is quasi-sinusoidal (after filtering). FIGS. 11 and 12 illustrate such a waveform in the time 210 and frequency 212 domains, respectively. This exemplary flow signal was sampled with $f_s$=100 Hz and processed using the DFT with N=500 points. The frequency domain representation of the signal 212 contains the instantaneous mean flow rate 214 along with a single additional prominent peak 216 located at a frequency 218 in hertz corresponding to the patient's heart rate in beats per minute divided by 60 seconds/minute. The peak 216 indicates the patient's heart rate and the peak-to-peak flow rate.

Figure 13:
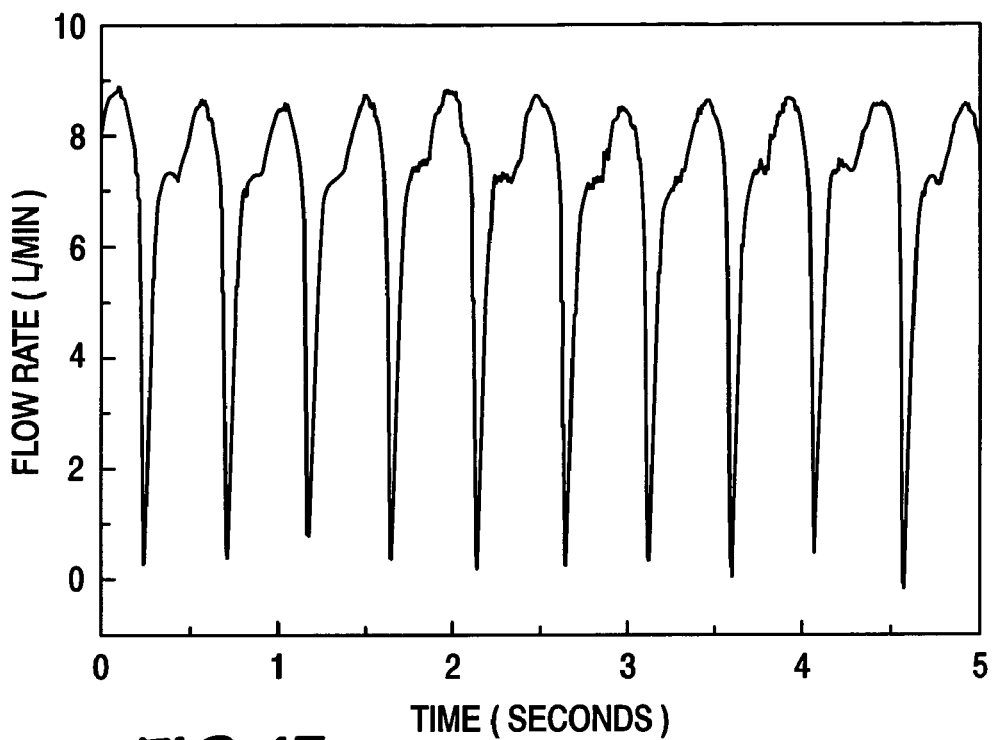
FIGS. 13 and 14 illustrate a distorted flow waveform (due to suction) in the time and frequency domains, respectively.
Figure 14:
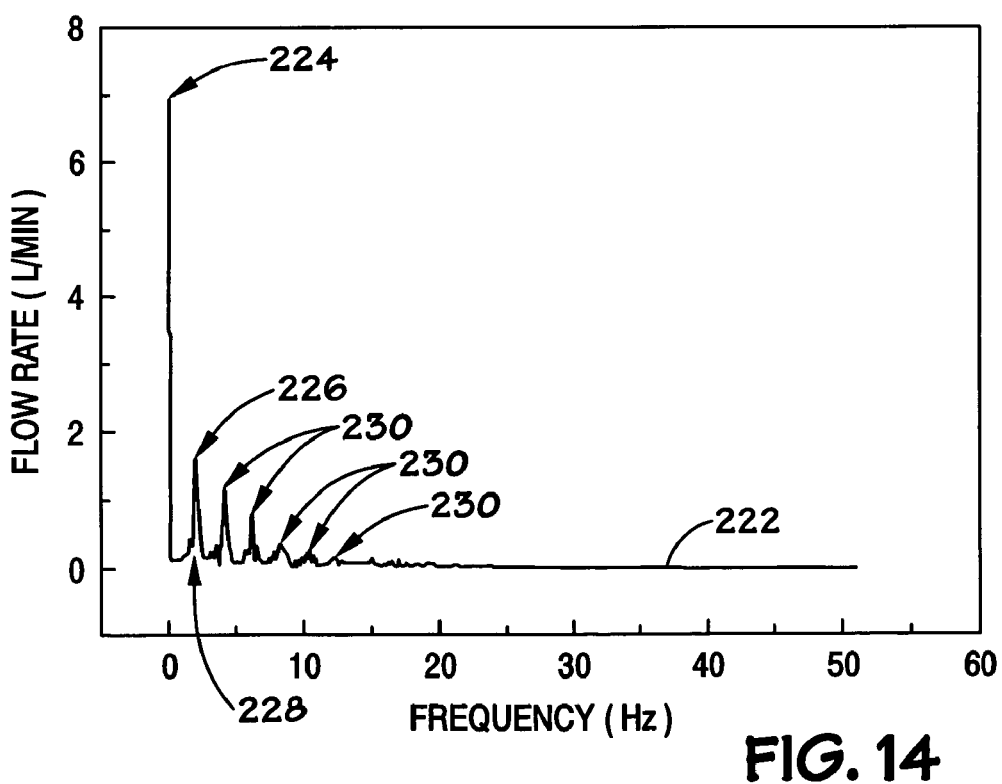

FIGS. 13 and 14 illustrate a distorted flow waveform due to suction in the time 220 and frequency 222 domains, respectively. As with the normal signal shown in FIGS. 11 and 12, the exemplary flow signal shown in FIGS. 13 and 14 was sampled with $f_s$=100 Hz and processed using the DFT with N=500 points. The frequency domain representation 222 of the signal contains the instantaneous mean flow rate 224, and multiple additional peaks located at a frequency proportional to the patient's heart rate and harmonics thereof. The peak 226 indicates the peak flow rate at the fundamental frequency 228, with additional peaks 230 at harmonics of the fundamental frequency 228. Transient suction events may contain additive frequency components which are not harmonically related to the fundamental frequency.

As noted herein above, the frequency domain representation 102 of the time continuous signal may be used to provide real-time parametric data, such as the patient's heart rate, and output to a user interface display 106, stored for later analysis, etc. Of course, an accurate heart rate determination can be critical to proper control of the pump system 10 and to the general management of a patient.

For example, determination of heart rate to ±1.5 BPM may be desired. Frequency resolution using the DFT or FFT algorithm is defined by the data sampling rate $f_s$ and the total number of samples to be processed N:

$$\frac{f_s}{N}.$$

This relationship indicates that the frequency resolution may be increased either by decreasing the data sampling rate or by increasing the total number of data points to be processed. The sampling rate $f_s$ must be sufficiently high to preserve the fidelity of the sampled flow signal (i.e. >60 Hz) and the number of samples N must be sufficiently low such that a new heart rate value is calculated in a timely fashion, for example, every one or two seconds.

In order for the FFT algorithm to calculate a heart rate value with an accuracy of ±1.5 BPM at a typical sampling rate $f_s$=100 Hz, 4096 data samples (N=4096) would be required. However, it would take 40.96 seconds to acquire 4096 samples with $f_s$=100. Thus, sampling 4096 data points clearly does not provide the required timeliness.

"Zero padding" consists of extending the sampled data with zeros to extend its time limits. It maps a length N signal to a length M signal, where M>N. To quickly and accurately determine heart rate, a relatively small data sample N is used, with the remaining time continuous signal sample points being zero padded. For example, one or two seconds of actual sampled time continuous data may be used to allow heart rate calculation within the desired time frame, resulting in 100 to 200 data points at $f_s$=100 Hz. The remaining 3896 to 3996 data points are zero padded to provide a quick and accurate heart rate calculation. A further increase or decrease in resolution may be obtained by increasing or decreasing the value of N, respectively. For example, a resolution of ±1 BPM may be obtained by using N=6000 data points with fs=100 Hz. In this instance, one to two seconds of actual time continuous data would be sampled, with 5800 to 5900 zero padded data points.

Figure 15:
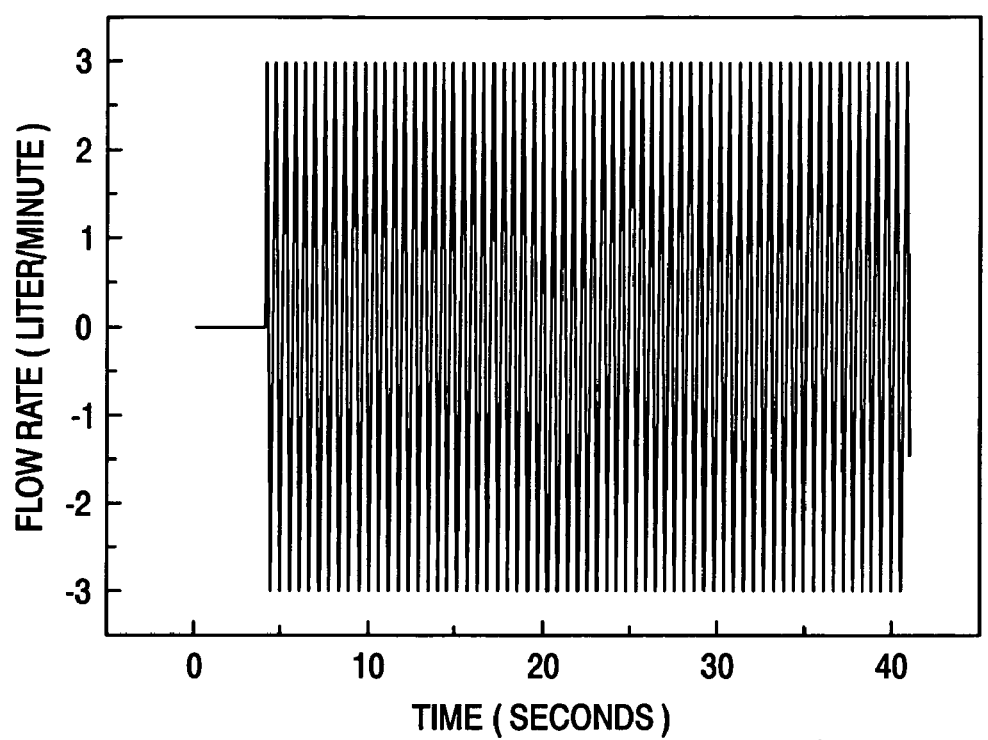
FIGS. 15 and 16 illustrate time domain representations of flow generated based on a sampling of a time continuous data using 10% and 90% zero padding, respectively.
Figure 16:
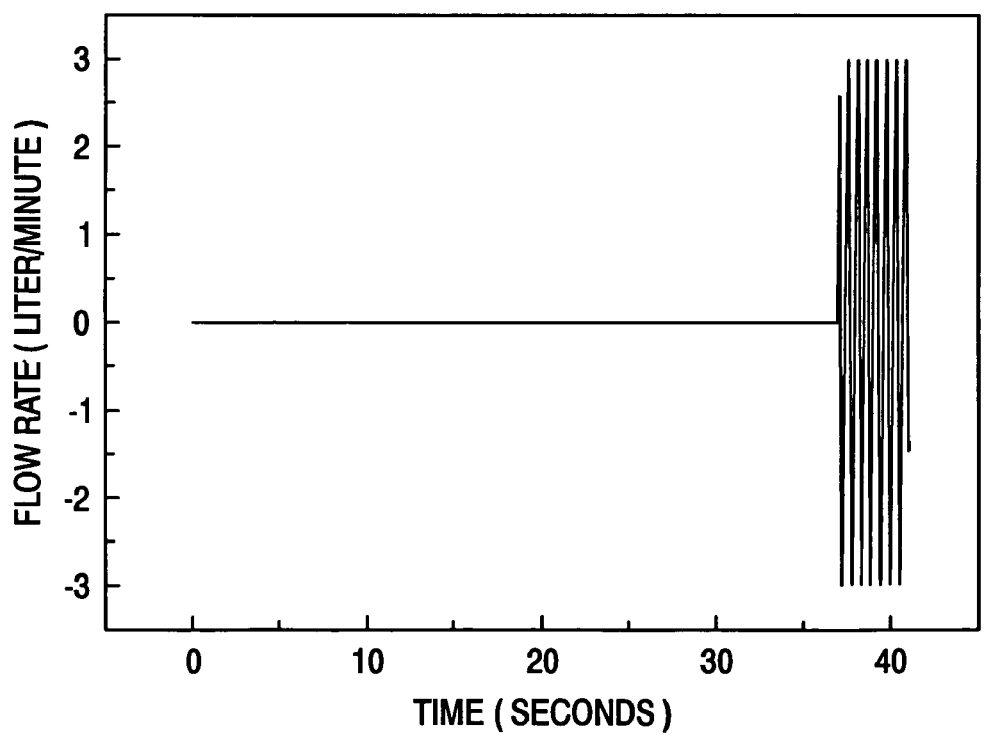
Figure 17:
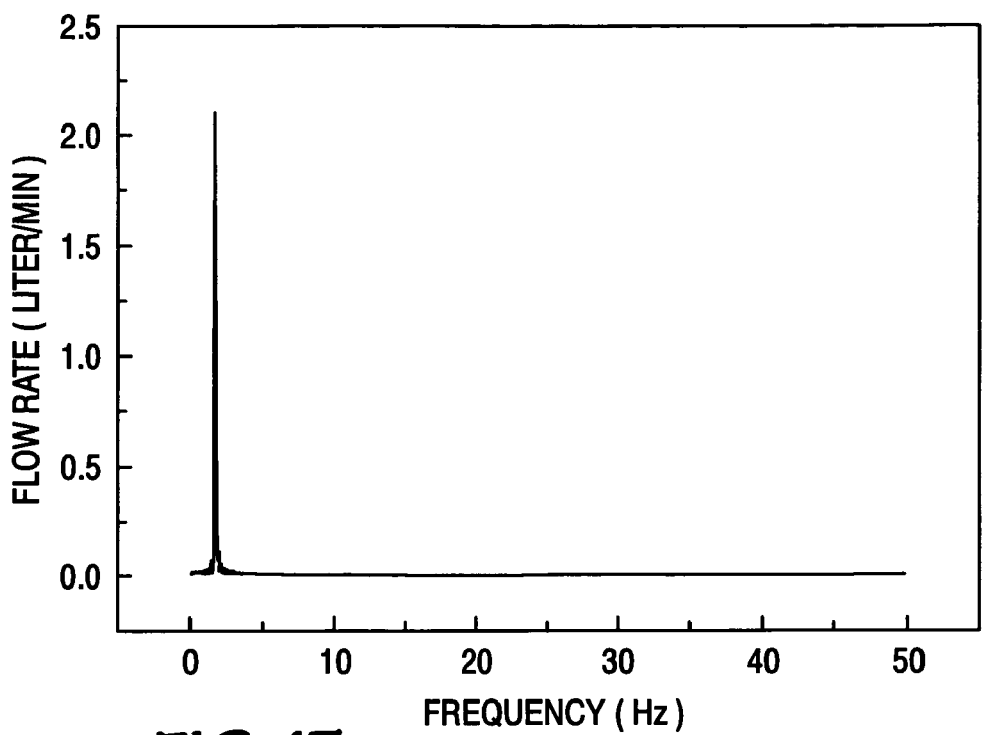
FIGS. 17 and 18 are frequency domain representations corresponding to the time domain representations shown in FIGS. 15 and 16, respectively.
Figure 18:
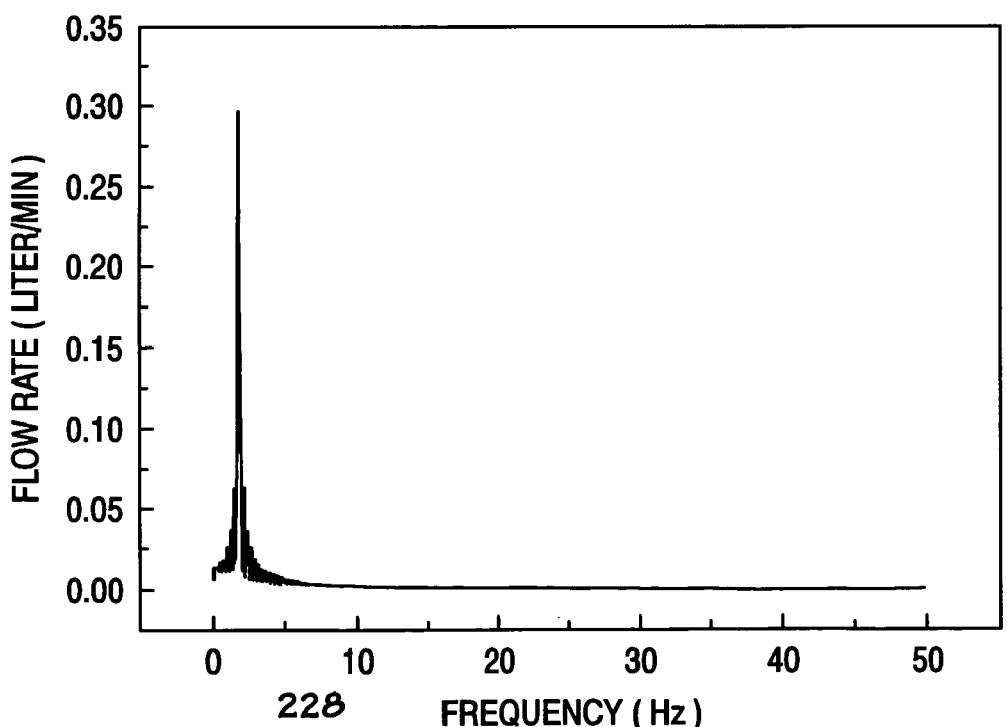

FIGS. 15 and 16 are time domain representations, and FIGS. 17 and 18 are corresponding frequency domain representations generated based on a sampling of a time continuous flow waveform using 10% and 90% zero padding, respectively. The flow waveform files upon which the illustrated frequency domain representations were based contained 4096 data points processed with the FFT algorithm. The synthesized signal used for this analysis was a sine wave sampled at fs=100 Hz with a mean flow rate of 3 liter/min, a peak-to-peak amplitude (pulsatility) of 6 liter/min, and a frequency of 1.772 Hz (106.3 BPM—a typical heart rate for a blood pump recipient). As noted above, the frequency resolution of the FFT algorithm is $$\frac{f_s}{N}.$$

Hence, the pulse rate resolution corresponding to these parameters is ±1.5 BPM.

As shown in FIGS. 17 and 18, the frequency resolution of the FFT algorithm in the frequency domain remains constant with 10% and 90% zero padding of the time domain data. Additional side lobes are generated with increased zero padding which further results in amplitude distortion at the fundamental frequency. However, the fundamental spectral component—which is proportional to heart rate—remains the most prominent in the FFT's resultant array. Since the objective is to determine heart rate, the amplitude distortion may be ignored and the correct heart rate may be obtained.

By using a single frequency domain representation of the sampled time continuous signal, a complete pump control system may be implemented onto one integrated circuit including signal validation, physiologic control, suction detection, motor control, and determination of parametric data such as heart rate.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of controlling a blood pump, comprising:
   sampling a time continuous signal from the blood pump;
   transforming the sampled time continuous signal to the frequency domain;
   analyzing the sampled time continuous signal in the frequency domain;
   controlling the blood pump in response to the analysis of the sampled time continuous signal in the frequency domain; and
   detecting excess suction in response to analysis of distortion in the sampled time continuous signal in the frequency domain.

2. The method of claim 1, further comprising determining parametric data in response to the analysis of the sampled time continuous signal in the frequency domain.

3. The method of claim 2, wherein the parametric data include heart rate.

4. The method of claim 3, further comprising zero padding the time continuous signal.

5. The method of claim 4, wherein sampling the time continuous signal from the blood pump includes sampling less than about 200 data points of the time continuous signal.

6. The method of claim 5, further comprising zero padding at least about 3800 data points.

7. The method of claim 2, wherein the parametric data include respiratory rate.

8. The method of claim 2, wherein the parametric data include pump flow rate.

9. The method of claim 1, further comprising validating the sampled time continuous signal in response to the analysis of the sampled time continuous signal in the frequency domain.

10. The method of claim 9, wherein validating the sampled time continuous signal includes evaluating the signal to noise ratio.

11. The method of claim 9, wherein validating the sampled time continuous signal includes evaluating the signal to noise plus distortion ratio.

12. The method of claim 1, wherein the time continuous signal comprises the pump flow rate.

13. The method of claim 1, wherein the time continuous signal comprises the pump speed.

14. The method of claim 1, wherein the time continuous signal comprises the pump current.

15. A blood pump control system, comprising:
a processor adapted to receive a time continuous signal from a blood pump; and
wherein the processor is programmed to transform the time continuous signal to the frequency domain, and to detect excess suction in response to distortion in the transformed time continuous signal.

16. The system of claim 15, wherein the processor is further programmed to determine parametric data based on the transformed time continuous signal, the processor including an output terminal for outputting the parametric data.

17. The system of claim 15, wherein the processor is programmed to validate the time continuous signal based on the transformed time continuous signal.

18. The system of claim 17, wherein the processor is programmed to calculate the signal to noise ratio of the transformed time continuous signal.

19. The system of claim 17, wherein the processor is programmed to calculate the signal to noise plus distortion ratio of the transformed time continuous signal.

20. The system of claim 15, further comprising a flow measurement device adapted to transduce the pump flow rate, and wherein the processor is adapted to receive a signal indicating the pump flow rate.

21. The system of claim 15, wherein the processor is connected to the pump to receive a signal indicating the pump speed.

22. The system of claim 15, wherein the processor is connected to the pump to receive a signal indicating the pump current.

23. The system of claim 15, farther comprising:
an analog to digital converter having a sampling rate and that digitizes at least a portion of the time continuous signal; and
a sample mode selector connected to the analog to digital converter, the sample mode selector setting one of a synchronous sample mode or an asynchronous sample mode, wherein
if the asynchronous sample mode is set, the sampling rate of the analog to digital converter is set by a reference clock; and
if the synchronous sample mode is set, the sampling rate of the analog to digital converter is set according to the frequency of the time continuous signal.

24. A blood pump system, comprising:
a blood pump comprising a rotor and a stator, the stator including a plurality of stator windings;
a controller operatively coupled to the pump;
a processor operatively coupled to the controller and adapted to receive a time continuous signal from the pump; and
wherein the processor is programmed to transform the time continuous signal to the frequency domain, and to detect excess suction in response to distortion in the transformed time continuous signal.

25. The blood pump system of claim 24, wherein the controller applies current to the stator windings in a sequence to create a rotating field, and wherein the time continuous signal includes one or more stator winding current.

26. The blood pump system of claim 24, further comprising a flow measurement device coupled to the processor and providing a signal representing the pump flow rate, wherein the time continuous signal includes the pump flow rate.

27. The blood pump system of claim 24, wherein the processor is programmed to zero pad a digital representation of the received time continuous signal.

28. The blood pump system of claim 27, wherein the digital representation of the received time continuous signal from the blood pump comprises less than about 200 data points of the time continuous signal.

29. The blood pump system of claim 28, wherein the processor is programmed to zero pad at least about 3800 data points.

30. A method of determining heart rate, comprising: sampling a time continuous signal from a blood pump at a predetermined sampling frequency for a predetermined time period to obtain a sample N; zero padding the sampled time continuous signal to achieve a sample M, where M is greater than N; transforming the zero padded time continuous signal to the frequency domain; and determining a heart rate based on the frequency domain representation.

31. The method of claim 30, wherein the frequency domain representation of the zero padded time continuous signal comprises a spectral peak at a frequency proportional to the heart rate.

* * * * *